United States Patent [19]

Miesel

[11] B 3,989,680

[45] Nov. 2, 1976

[54] 3,3-DIALKYL-1-(SUBSTITUTED-PHENYL) TRIAZENE-1-OXIDES

[75] Inventor: John L. Miesel, Indianapolis, Ind.

[73] Assignee: Eli Lilly and Company, Indianapolis, Ind.

[22] Filed: Sept. 6, 1974

[21] Appl. No.: 503,579

[44] Published under the second Trial Voluntary Protest Program on February 10, 1976 as document No. B 503,579.

[52] U.S. Cl. .............................. 260/140 R; 424/226
[51] Int. Cl.$^2$ ....................................... C07C 107/04
[58] Field of Search ..................... 260/140; 424/226

[56] References Cited
UNITED STATES PATENTS

| | | | |
|---|---|---|---|
| 3,138,521 | 6/1964 | Jelinek et al. | 260/140 X |
| 3,206,357 | 9/1965 | Cannon et al. | 260/140 X |
| 3,714,351 | 1/1973 | Gubler | 424/226 |

FOREIGN PATENTS OR APPLICATIONS

| | | | |
|---|---|---|---|
| 791,322 | 5/1973 | Belgium | 260/140 |
| 2,147,259 | 3/1972 | Germany | 424/226 |
| 1,130,469 | 10/1968 | United Kingdom | 260/140 |

OTHER PUBLICATIONS

Behera et al., Spectrochim. Acta, Part A, 1971, 27(10), pp. 2273–2275.
Chakrauorty et al., Chemical Abstracts, vol. 75 (1971).
Behera et al., Chemical Abstracts, vol. 75 (1971).

*Primary Examiner*—Charles F. Warren
*Attorney, Agent, or Firm*—Walter E. Buting; Everet F. Smith

[57] ABSTRACT

3,3-Dialkyl-1-(substituted-phenyl)triazene-1-oxides and N-phenylazo heterocyclic compounds having anti-inflammatory properties.

12 Claims, No Drawings

3,3-DIALKYL-1-(SUBSTITUTED-PHENYL) TRIAZENE-1-OXIDES

BACKGROUND OF THE INVENTION

The etiology and pathogenesis of rheumatic and arthritic diseases remain obscure. Meanwhile, the need continues for safer, better tolerated drugs which will slow the progress and alleviate the symptoms of inflammatory diseases. For example, in rheumatoid arthritis any agent which reduces the inflammation is important in lessening or delaying the development of crippling.

The 3,3-dialkyl-1-(substituted-phenyl)triazene-1-oxides of the present invention represent a novel class of nonsteroidal compounds useful in the treatment of the inflammatory process.

Compounds related to those of the present invention include a class of 3-(substituted-phenyl)-1-alkyltriazene-1-oxides described as insecticides in Belgian Pat. No. 744930. Compounds of said patent are actually described as 1-(substituted-phenyl)-3-alkyl-3-hydroxy-triazenes, but similar compounds are proven in Tetrahedron Letters No. 30, pp. 2593–2596 (1965) to be predominantly the 3-(substituted-phenyl)-1-alkyltriazene-1-oxide isomers. The order of numbering of the position of substituents on triazene-oxides and hydroxytriazenes is reversed.

Triazene-1-oxides are readily prepared by those skilled in the art. The method of preparation listed in Beilstein XVI, 742 and similar to that employed in the present invention, consists of reacting an unsymmetrical hydrazine, namely α-methyl-α-phenylhydrazine or α-diphenylhydrazine, with a substituted nitrosobenzene.

The 1-(substituted-phenyl)-3-hydroxy-3-methyltriazenes, isomeric to 3-(substituted-phenyl)-1-methyltriazene-1-oxides, are also described in Belgian Pat. No. 791,322 as immunosupressive agents. The method of preparation described therein consists of reacting an aniline with nitrous acid followed by a hydroxylamine. All of the above mentioned compounds differ from the compounds of the present invention in the position of attachment on the triazene of the substituted phenyl and alkyl groups.

SUMMARY OF THE INVENTION

This invention relates to 3,3-dialkyl-1-(substituted-phenyl)triazene-1-oxides which have desirable anti-inflammatory properties. More particularly this invention provides 3,3-dialkyl-1-(mono- or disubstituted-phenyl)triazene-1-oxides of the formula

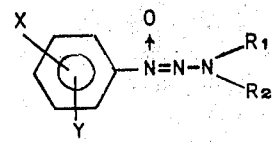

wherein X is hydrogen, halo, nitro, $C_1$-$C_3$ lower alkoxy, $C_1$-$C_3$-lower dialkylamino, trihalomethyl or $C_1$-$C_3$ lower alkyl, Y is hydrogen, halo, $C_1$-$C_3$ lower alkoxy, or $C_1$-$C_3$ lower alkyl; $R_1$ and $R_2$ taken separately are $C_1$-$C_3$ lower alkyl; or $R_1$ and $R_2$ taken together with the nitrogen to which they are attached are piperidino $C_1$-$C_3$-alkylpiperidino, di-$C_1$-$C_3$-alkylpiperidino, morpholino, or 3-(2-oxo-oxazolidino).

DETAILED DESCRIPTION

The reaction sequence for preparation of the compounds of the present invention is represented by the following equations.

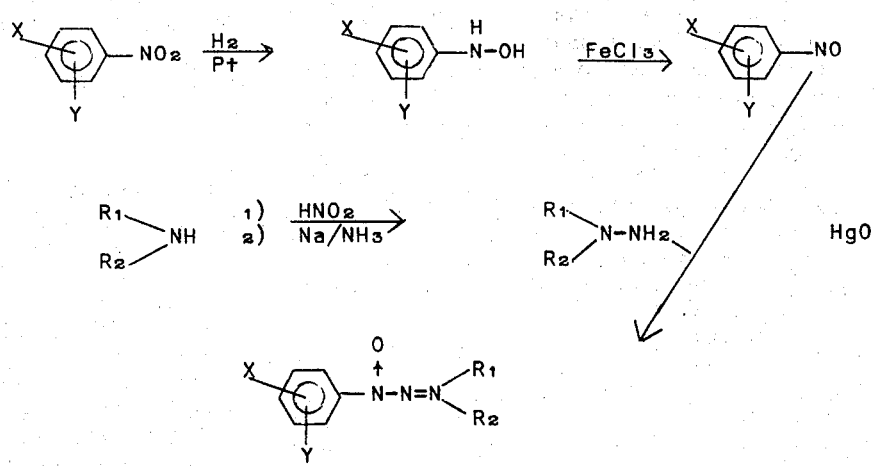

Compounds of the present invention are prepared using a substituted nitrosobenzene, which may be prepared from the corresponding nitro compound by reduction to the substituted phenylhydroxylamine, using a reducing agent such as zinc dust followed by oxidation under conditions such as chromic acid, Org. Syn., 25, 80 (1945). Substituted phenylhydroxylamines are alternatively and preferably prepared by catalytic reduction of the corresponding nitrobenzenes under suitable conditions. More preferably the reduction is accomplished by hydrogenating using a suitable catalyst such as platinum oxide in the presence of DMSO. Paul N. Rylander, 3rd Conference on Catalytic Hydrogenation, New York Academy of Sciences, 172, 266.

The oxidation of the substituted phenylhydroxylamine is preferably carried out using ferric chloride in dilute sulfuric acid. J.O.C., 2, 73 (1937) and J. Chem. Soc., 773 (1939).

Unsymmetrical dimethylhydrazine is available commercially. Other unsymmetrical disubstituted hydrazines are conveniently prepared by nitrosation of secondary amines followed by reduction to the hydrazines, as described in J. Am. Chem. Soc., 77, 790-793 (1955) and Zhur. Obshchei. Khim., 28, 1296-1302 (1958).

The unsymmetrical disubstituted hydrazine is added to a mixture of the substituted-nitrosobenzene and mercuric oxide in an appropriate inert solvent such as ethyl acetate or ethanol at 0°C. The reaction is complete after standing at ambient temperature for a period of 16 hours. The 3,3-dialkyl-1-substituted triazene-1-oxide is isolated by filtering the reaction mixture and concentrating the filtrate. Chromatography is preferable for purification.

Use of the mercuric oxide is optional, but incorporation of the mercuric oxide eliminates the need of addition of an extra molar equivalent of the substituted nitrosobenzene. When the mercuric oxide is omitted one half of the nitrosobenzene employed in the reaction is utilized as an oxidant.

In the isolation of the triazene-1-oxide the product may be separated from the azoxy compound, formed as a by-product, by chromatography in an appropriate solvent and/or crystallization from the appropriate solvent.

The substituted phenyl groups employed in the present invention include phenyl, chlorophenyl, $C_1$-$C_3$ alkylphenyl, $C_1$-$C_3$ alkoxyphenyl, nitrophenyl, dichlorophenyl, difluorophenyl, chloro-m-bromophenyl, di-$C_1$-$C_3$ lower alkoxyphenyl, di-$C_1$-$C_3$ alkylaminophenyl, di-$C_1$-$C_3$ lower dialkylphenyl and the like.

The term "$C_1$-$C_3$ lower alkoxy" refers to methoxy, ethoxy, n-propoxy, isopropoxy. The term "$C_1$-$C_3$ lower dialkylamino" refers to dimethylamino, diethylamino, di-n-propylamino, diisopropylamino, methylethylamino, methyl-n-propylamino, and the like. The term "halo" refers to fluoro, chloro, bromo, and iodo.

Compounds of this invention are effective in treating inflammatory disorders and are orally administered to a warm-blooded animal at doses ranging from 1 to 100 mg./kg. of animal body weight. In the antiinflammatory assay, a modification of the Winder method was used to measure the anti-inflammatory activities of the instant triazene-oxides [Winder, C. V.; Wax. J.; Burr, V.; Been, M.; and Posiere, C. E.; A Study of Pharmacological Influences on Ultraviolet Erythema in Guinea Pigs. *Arch. Int. Pharmcodyn.* 116, 261 (1958)]. Albino guinea pigs of either sex, weighing 225–300 grams, were shaved on the back and chemically depilated 18–20 hours before exposure to ultraviolet light (Nair, Lotion Hair Remover, Carter Products, N.Y., N.Y.). The animals were fasted overnight. A group of 48 animals bearing identifying ear tags were dosed by means of an oral dosing needle. The drugs administered as suspensions in 1 to 2 cc. of methyl cellulose (Methocell, Dow). The control treatment consisted of administering drug vehicle, Methocell, to a group of four animals. A positive control treatment consisted of giving four animals an effective dose of fenoprofen, 2-(3-phenoxyphenyl)propionic acid. Ten groups of four animals each were given different dose levels of test compound to obtain dose-responses. Random order and blind administration of the drugs were employed. Forth-eight of the animals were graded and drug identification was made after the animals were graded. The test was invalid if the animals did not respond to fenoprofen. Immediately after the guinea pigs were treated, a gummed notebook paper reinforcement was placed on their back, and they were exposed to a high intensity ultraviolet light for 7 seconds. The ultraviolet light source, a Hanovia Lamp (Kromayer-Model 10), was used to irradiate the skin of the guinea pig's back. After exposure, the reinforcements were removed, and the back was wiped clean with a water-soaked gauze sponge. The unexposed area under the reinforcement provided an area of contrast for grading the erythema. Beginning one hour after exposure and thereafter at half-hour intervals for another 1 ½ hours, the degree of resulting erythema was graded by an arbitrary scoring system based upon the degree of contrast and redness formed. Anti-inflammatory agents delay the development of the erythema and have their greatest effect at the initial grading periods. The scores were, therefore, weighted by factors of 4, 3, 2, and 1 at the 1.0, 1.5, 2.0, and 2.5 hour scoring times, respectively. The erythema was graded as follows:

| Score | Erythema Scoring System Appearance of Exposed Area |
|---|---|
| 0 | No redness and no contrast |
| 1 | Slight redness with a faint reinforcement outline |
| 2 | Slight to moderate redness with a distinct outline. |
| 3 | Marked redness with a distinct circular outline |

Total scores from each treatment group of four guinea pigs were compared to the control treatment and the percent inhibition, calculated as follows:

$$100 \times \frac{\text{Control Score} - \text{Treatment Score}}{\text{Control Score}} = \text{Percent Inhibition}$$

A dose-response graph was obtained by plotting dose versus percent inhibition, the points representing the average of each treatment group of four guinea pigs. The dose ($ED_{50}$) in milligrams per kilogram (mg./kg.) of animal body weight which produced a 50 percent inhibition of the erythemic response for the particular compound tested was obtained by extrapolation. Tables I and II below summarize the results obtained from testing representative compounds of the invention by the foregoing method. The plotted dose ($ED_{50}$) which represents a 50% inhibition of the erythemic response for the particular compound tested is given in the last column of Tables I and II.

Table I

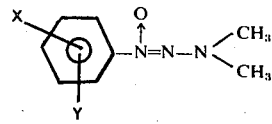

| X | Y | Inhibition 50 mg./kg. | (Estimated) E.D. 50 mg./kg. |
|---|---|---|---|
| H | H | 96% | 7.5 |
| o-Cl | H | 81% | 24 |
| m-Cl | H | 100% | 17 |
| p-Cl | H | 82% | 27 |
| o-$CH_3$ | H | 97% | 9.0 |
| 2-$CH_3$ | 3-$CH_3$ | 64% | — |
| m-$CF_3$ | H | 90% | 16.5 |
| m-$NO_2$ | H | 54% | 50 |
| p-$N(CH_3)_2$ | H | 42% | — |
| p-$OCH_3$ | H | 79% | 28 |
| o-F | H | 88% | 16 |

Table II $$\underset{Y}{\overset{X}{\diagdown}}\text{C}_6\text{H}_3-N=N-N\overset{O}{\diagdown}Z$$

| X | Y | Z | Inhibition 50 mg./kg. | (Estimated) E.D. 50 mg./kg. |
|---|---|---|---|---|
| H | H | 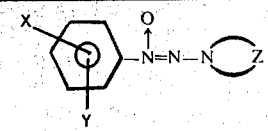 | 52% | 23 |
| H | H |  | 47% | 47 |
| H | H | 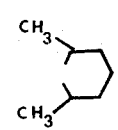 | 62% | 42 |

Compounds of the present invention possess interesting pharmacological activities other than anti-inflammatory results. Among those desirable properties which the compounds possess are anti-microbial and anit-fungal activities, and three of the compounds, 3,3-dimethyl-1-(2,3-dimethylphenyl)triazene-1-oxide, 3,3-dimethyl-1-(3-trifluoromethylphenyl)triazene-1-oxide, and 3,3-dimethyl-1-(3-nitrophenyl)triazene-1-oxide, additionally possess neurosedative properties.

Illustrative compounds of the present invention are as follows:

3,3-dimethyl-1-phenyltriazene-1 oxide,
3,3-diethyl-1-phenyltriazene-1-oxide,
4-(O,N,N-phenylazoxy)morpholine,
3-isopropyl-3-methyl-1-phenyltriazene-1-oxide,
3,3-dimethyl-1-(o-tolyl)triazene-1-oxide,
3,3-dimethyl-1-(m-nitrophenyl)triazene-1-oxide,
3,3-dimethyl-1-(m-trifluoromethylphenyl)triazene-1-oxide,
3,3-diisopropyl-1-(m-nitrophenyl)triazene-1-oxide,
3-n-propyl-3-methyl-1-(m-iodophenyl)triazene-1-oxide,
3,3-di-n-propyl-1-(m-bromophenyl)triazene-1-oxide,
3,3-dimethyl-1-(p-methoxyphenyl)triazene-1-oxide,
3,3-diethyl-1-(p-methoxyphenyl)triazene-1-oxide,
3,3-dimethyl-1-(m-chlorophenyl)triazene-1-oxide,
3,3-diisopropyl-1-(p-chlorophenyl)triazene-1-oxide,
3,3-dimethyl-1-(p-dimethylaminophenyl)triazene-1-oxide,
1-(O,N,N-phenylazoxy)-2,6-dimethylpiperidine,
1-(O,N,N-phenylazoxy)-4-methylpiperidine,
3-n-propyl-3-ethyl-1-(p-tribromomethylphenyl)triazene-1-oxide,
3-isopropyl-3-methyl-1-(o-trichloromethylphenyl)-triazene-1-oxide,
3-ethyl-3-methyl-1-(o-chlorophenyl)triazene-1-oxide,
4-(O,N,N-phenylazoxy)morpholine,
3-(O,N,N-phenylazoxy)-2-oxazolidinone,
3,3-dimethyl-1-(o-fluorophenyl)triazene-1-oxide,
3,3-dimethyl-1-(o-chlorophenyl)triazene-1-oxide,
3,3-di-n-propyl-1-(o-ethoxyphenyl)triazene-1-oxide,
4-(O,N,N-p-isopropylphenylazoxy)morpholine,
3,3-diethyl-1-(o-n-propylphenyl)triazene-1-oxide,
3-(O,N,N-m-methoxyphenylazoxy)-2-oxazolidinone,
3,3-dimethyl-1-(2,3-dimethylphenyl)triazene-1-oxide,
1-(O,N,N-phenylazoxy)-3,4-dimethylpiperidine,
1-(O,N,N-p-iodophenylazoxy)-3-propylpiperidine,
1-(O,N,N-o-fluorophenylazoxy)-2,5-diethylpiperidine,
1-(O,N,N-2,5-dichlorophenylazoxy)-4,4-dimethylpiperidine,
1-(O,N,N-3,4-dimethoxyphenylazoxy)-3,3-dimethylpiperidine,
1-(O,N,N-3-diethylaminophenylazoxy)-2-n-propylpiperidine,
3,3-di-n-propyl-1-(p-n-propoxyphenyl)triazene-1-oxide,
3,3-diisopropyl-1-(o-isopropoxyphenyl)-triazene-1-oxide,
1-(O,N,N-2,5-dibromophenylazoxy)-2-isopropylpiperidine, and the like.

The preparation of compounds is further exemplified by the following examples.

EXAMPLE 1

3,3-Dimethyl-1-phenyltriazene-1-oxide.

To a solution of 7.5 g. of nitrosobenzene in 80 ml. of ethanol at 0° was added in a dropwise manner 4.2 g. of unsymmetrical-dimethylhydrazine as a saturated solution in ethanol. After stirring at 0° for 2 hours, the reaction mixture was allowed to warm to 25° C. and stirred for 16 hours longer. The solution was concentrated in vacuo, and the red-brown oil was chromatographed on silica gel in benzene. The product was eluted with 5–10 percent ethyl acetate in benzene. Three grams of 3,3-dimethyl-1-phenyltriazene-1-oxide was obtained as a light brown oil which gave a suitable n.m.r. spectrum.

Analysis, calculated for $C_8H_{11}N_3O$ (in percent):
C, 58.14; H, 6.71; N, 55.44.
Found: C, 58.42; H, 6.92; N, 55.58.

According to the above procedure, nitrosobenzene was reacted with 1-aminopiperidine to yield 1-(O,N,N-phenylazoxy)-piperidine.

EXAMPLE 2

3,3-Dimethyl-1-(o-tolyl)triazene-1-oxide.

To a suspension of 6.0 g. of o-nitrosotoluene in 250 ml. of ethanol at 0° was added 21.7 g. of mercuric oxide. To this reaction mixture was added dropwise 3.0 g. of unsymmetrical-dimethylhydrazine in 50 ml. of ethanol. The mixture was stirred at 0°–5°C. for 2 hours, then at 25°C. for 16 hours. The mixture was filtered through infusorial earth, and the solvent was evaporated. The crude orange-red oil was chromatographed on 300 ml. of silica gel in benzene. Elution with 10 percent ethyl acetate in benzene gave 3.7 g. of 3,3-dimethyl-1-(o-tolyl)-triazene-1-oxide as an oil. The n.m.r. spectrum was satisfactory.

Analysis, calculated for $C_9H_{13}N_3O$ (in percent):
C, 60.32; H, 7.31; N, 23.45.
Found: C, 60.11; H, 7.09; N, 23.20.

According to the above procedure using unsymmetrical dimethylhydrazine and substituted nitrosobenzenes, the following products were prepared:

m-Nitronitrosobenzene gave 3,3-dimethyl-1-(m-nitrophenyl 1-oxide, m.p. 77°–78°C.

Analysis, calculated for $C_8H_{10}N_4O_3$ (in percent):
C, 45.71; H, 4.88; N, 26.66.
Found: C, 45.85; H, 5.14; N, 26.91.
N.m.r. was suitable for the structure.

m-Trifluoromethylnitrosobenzene gave 3,3-dimethyl-1-(m-trifluoromethylphenyl)triazene-1-oxide.

Analysis, calculated for $C_9H_{10}F_3N_3O$ (in percent):
C, 46.36; H, 4.32; N, 18.02.
Found: C, 46.29; H, 4.15; N, 17.84.
The n.m.r. was suitable for the structure.

p-Methoxynitrosobenzene gave 3,3-dimethyl-1-(p-methoxyphenyl)triazene-1-oxide.

Analysis, calculated for $C_9H_{13}N_3O_2$ (in percent):
C, 55.37; H, 6.71; N, 21.52.
Found: C, 55.25; H, 6.64; N, 21.38.
The n.m.r. spectrum was suitable for the desired compound.

m-Chloronitrosobenzene gave 3,3-dimethyl-1-(m-chlorophenyl)triazene-1-oxide.

Analysis, calculated for $C_8H_{10}ClN_3O$ (in percent):
C, 48.13; H, 5.05; N, 21.05,
Found: C, 48.12; H, 4.87; N, 21.32.
The n.m.r. spectrum was satisfactory.

p-Chloronitrosobenzene gave 3,3-dimethyl-1-p-chlorophenyl)triazene-1-oxide.
m.p. 42°–45°C.

Analysis, calculated for $C_8H_{10}ClN_3O$ (in percent):
C, 48.12; H, 5.01; N, 21.05.
Found: C, 48.25; H, 4.83; N, 21.24.

EXAMPLE 3

3,3-Dimethyl-1-(p-dimethylaminophenyl)triazene-1-oxide.

To a suspension of 7.5 g. of p-dimethylaminonitrosobenzene in 250 ml. of ethanol at 0°C. was added 21.7 g. of mercuric oxide. To this mixture at 0°C. was added dropwise 3.3 g. of unsymmetrical dimethylhydrazine in 50 ml. of ethanol. After stirring one hour at 0°C. and 16 hours at 25°C., the mixture was filtered through infusorial earth, and the filtrate was concentrated to an orange-colored oil. The material was separated on a column of grade IV silica in ether, using high pressure column chromatography. Three and one tenth grams of material was obtained by concentrating the pooled eluant from the column and was recrystallized to give 2.65 g. of 3,3-dimethyl-1-(p-dimethylaminophenyl)-triazene-1-oxide as yellow needles, m.p. 79°–80°C.

Analysis, calculated for $C_{10}H_{16}N_4O$ (in percent):
C, 57.67; H, 7.74; N, 26.90.
Found: C, 57.69; H, 7.58; N, 27.09.

EXAMPLE 4

1-(O,N,N-phenylazoxy)-2,6-dimethylpiperidine.

To a stirred solution of 5.35 g. of nitrosobenzene and 21.7 g. of mercuric oxide in 200 ml. of ethyl acetate at 0° was added dropwise 6.4 g. of 1-amino-2,6-dimethylpiperidine in 50 ml. of ethyl acetate. After being stirred for 2 hours at 0°C. and 16 hours at 25°C., the mixture was filtered through infusorial earth and concentrated to give a dark oil. Chromatography on silica gel using benzene ethyl acetate gave 8.3 g. of 1-(O,N,N,-phenylazoxy)-2,6-dimethylpiperidine as an orange-brown oil.

Analysis, calculated for $C_{13}H_{19}N_3O$ (in percent):
C, 66.92; H, 8.21; N, 18.01.
Found: C, 66.79; H, 8.17; N. 17.81.

The n.m.r. spectrum was suitable for the product.

Using the above procedure and nitrosobenzene with 4-aminomorpholine afforded 4-(O,N,N-phenylazoxy)-morpholine, m.p. 48°–50°C.

Analysis, calculated for $C_{10}H_{13}N_3O_2$ (in percent):
C, 57.96; H, 6.32; N, 20.28.
Found: C, 58.29; H, 6.03; N, 20.37.

EXAMPLE 5

3-(O,N,N-Phenylazoxy)-2-oxazolidinone.

To a stirred mixture of 5.35 g. of nitrosobenzene and 21.7 g. of yellow mercuric oxide in 200 ml. of ethyl acetate at 0°C. was added dropwise 5.1 g. of 3-amino-2-oxazolidinone in 100 ml. of ethyl acetate. After stirring at 25°C. for 16 hours, the reaction mixture was filtered through infusorial earth, the filtrate was concentrated and the residue was crystallized from ethanol to give 7.7 g. of 3-(O,N,N,-phenylazoxy)-2-oxazolidinone as almost colorless needles, m.p. 97°–99°C.

Analysis, calculated for $C_9H_9N_3O_3$ (in percent):
C, 52.17; H, 4.38; N, 20.28.
Found: C, 52.06; H, 4.29; N, 20.47.
N.m.r. spectrum was satisfactory.

EXAMPLE 6

3,3-Dimethyl-1-(o-fluorophenyl)triazene-1-oxide.

A solution of 14.1 g. of o-fluoronitrobenzene in 175 ml. of ethanol and 25 ml. of dimethyl sulfoxide was hydrogenated using 350 mg. of platinum oxide until two equivalents of hydrogen were taken up. The solution of o-fluorophenylhydroxylamine was poured into a solution of 32.5 g. of ferric chloride in 500 ml. of water containing 18 ml. of sulfuric acid at 0°C. After being stirred for 30 minutes, the mixture was shaken with ether and the water was separated. The etheral solution was dried and concentrated to give 10.0 g. of crude o-fluoronitrosobenzene. This was dissolved in 250 ml. of ethyl acetate, cooled to 0°C., and 35.0 g. of mercuric oxide was added. Then 4.8 g. of dimethylhydrazine in 50 ml. of ethyl acetate was added in a dropwise fashion. The mixture was stirred 16 hours at 25°C. and was then filtered through infusorial earth. The filtrate was concentrated and chromatographed on 300 ml of silica in benzene. The product was eluted with ethyl acetate in benzene. One and seven tenths grams of 3,3-dimethyl-1-(o-fluorophenyl)triazene-1-oxide was obtained as a brown oil which gave a satisfactory n.m.r. spectrum.

Analysis, calculated for $C_8H_{10}FN_3O$ (in percent):
C, 52.45; H, 5.50; N, 22.94.
Found: C, 52.38; H, 5.25; N, 22.74.

According to the procedure above o-chloronitrobenzene was hydrogenated to o-chlorophenylhydroxylamine and oxidized with ferric chloride to the nitroso compound. The nitroso derivative was then treated wth unsymmetrical dimethylhydrazine to yield 1-(o-chlorophenyl)-3,3-dimethyl-triazene-1-oxide which had the appropriate n.m.r. spectrum.

Analysis calculated for $C_8H_{10}ClN_3O$ (in percent):
C, 48.13; H, 5.05; N, 21.05;
Found: C, 48.23; H, 4.83; N, 20.88.

Similarly 12.1 g. of 2,3-dimethylnitrobenzene was hydrogenated to 2,3-dimethylphenylhydroxylamine, which was oxidized with ferric chloride to the nitroso compound. This compound was treated with unsymmetrical dimethylhydrazine to yield 3,3-dimethyl-1-(2,3-dimethylphenyl)triazene-1-oxide.

Analysis, calculated for $C_{10}H_{15}N_3O$ (in percent):
C, 62.15; H, 7.82; N, 21.74.

Found: C, 61.90; H, 7.70; N, 21.45.
The n.m.r. spectrum was satisfactory.

I claim:
1. A compound of the formula:

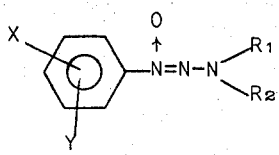

wherein $R_1$ and $R_2$ taken separately are $C_1$-$C_3$ alkyl or $R_1$ and $R_2$ taken together with the nitrogen to which they are attached form a heterocyclic group selected from the class consisting of piperidino, $C_1$-$C_3$ alkyl-piperidino, di-($C_1$-$C_3$ alkyl)piperidino, morpholino, and 3-(2-oxo-oxazolidino);
X is hydrogen, halo, nitro, $C_1$-$C_3$ lower alkoxy, $C_1$-$C_3$ lower dialkylamino, trifluoromethyl or $C_1$-$C_3$ lower alkyl, and Y is hydrogen, $C_1$-$C_3$ lower alkyl, halo or $C_1$-$C_3$ lower alkoxy.

2. The compound of claim 1, said compound being 3,3-dimethyl-1-phenyltriazene-1-oxide.
3. The compound of claim 1 wherein X is halo and Y is hydrogen.
4. The compound of claim 3, said compound being 3,3-dimethyl-1-(2-chlorophenyltriazene)-1-oxide.
5. The compound of claim 3, said compound being 3,3-dimethyl-1-(3-chlorophenyltriazene)-1-oxide.
6. The compound of claim 3, said compound being 3,3-dimethyl-1-(4-chlorophenyltriazene)-1-oxide.
7. The compound of claim 1, said compound being 3,3-dimethyl-1-(4-o-methoxyphenyltriazene)-1-oxide.
8. The compound of claim 1, said compound being 3,3-dimethyl-1-(3-trifluoromethyltriazene)-1-oxide.
9. The compound of claim 1, said compound being 3,3-dimethyl-1-(2,3-dimethylphenyl)triazene-1-oxide.
10. The compound of claim 1, said compound being 3,3-dimethyl-1-(3-nitrophenyltriazene)-1-oxide.
11. The compound of claim 1, said compound being 3,3-dimethyl-1-(4-p-methoxyphenyl)triazene-1-oxide.
12. The compound of claim 1, said compound being 1-(O,N,N-phenylazoxy)-2,6-dimethylpiperidine.

* * * * *